United States Patent [19]

Fujita et al.

[11] Patent Number: 4,577,032
[45] Date of Patent: Mar. 18, 1986

[54] 1-BENZOYLDIBROMOMETHYL-2-METHYLIMIDAZOLE AS A FUNGICIDAL AGENT

[76] Inventors: Takayuki Fujita, 233-8, Aza Inamoto, Nakakirai, Matsushige-cho, Itano-gun, Tokushima-ken; Yoshikazu Kitazawa, 42-1, Aza Kowake, Ejiri, Kitajima-cho, Itano-gun, Tolushima-ken; Tadashi Akita, 2-3, Hachiban-cho, Sako, Tokushima-shi, Tokushima-ken; Isamu Tani, 344-2, Myodo-cho 1-chome,, Tokushima-shi, Tokushima-ken, all of Japan

[21] Appl. No.: 621,104

[22] Filed: Jun. 15, 1984

[51] Int. Cl.$^4$ .................................. C07D 233/60
[52] U.S. Cl. ........................................ 548/341
[58] Field of Search ........................ 548/341

[56] References Cited

U.S. PATENT DOCUMENTS 4,389,409  6/1983  Miller .................................. 548/341

FOREIGN PATENT DOCUMENTS 2937595  4/1981  Fed. Rep. of Germany ...... 548/341

OTHER PUBLICATIONS

*Dorland's Illustrated Medical Dictionary*, 26th Edit., 1981, p. 1370.
Physician's Desk Reference, 5th Edit., 1984, pp. 632–633 and 671–672.
Streitwieser et al., "Intro. to Organic Chemistry," 2nd Ed., 1981, pp. 104–105.

*Primary Examiner*—Richard A. Schwartz
*Assistant Examiner*—Kurt G. Briscoe
*Attorney, Agent, or Firm*—Barry Kramer; Frederick H. Rabin

[57] ABSTRACT

This invention relates to 1-benzoylhalomethylimidazole compounds and processes for their production.

The 1-benzoylhalomethylimidazole compounds are represented by the following formula:

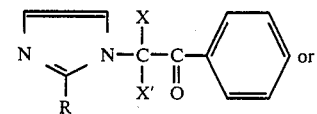

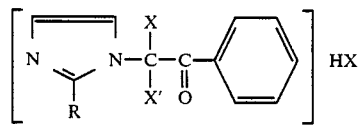

wherein R is a hydrogen atom or a lower alkyl group, X is a halogen atom and X' is a hydrogen atom or a halogen atom. They are very useful as antifungal agents, insect attractants and the like.

1 Claim, No Drawings

1-BENZOYLDIBROMOMETHYL-2-METHYLIMIDAZOLE AS A FUNGICIDAL AGENT

BACKGROUND OF THE INVENTION

1. Field of the Invention

This invention relates to novel 1-benzoylhalomethylimidazole compounds and processes for their production.

These imidazole compounds according to this invention can be used effectively as a fungicide.

2. Prior Art

It has already been known that some types of imidazole compounds have fungicidal properties.

For example, as fungicides for agricultural and horticultural purposes, Japanese Examined Patent Publication No. 43-16479 discloses compounds such as 1-hydroxyethyl-2-undecyl-3-methylimidazolium-p-toluensulfonate, 1-benzyl-2-undecyl-3-methylimidazolium-methylsulfate, 1-dodecyl-2-ethyl-3-benzylimidazolium chloride, and other similar imidazole compounds.

As compared with these compounds, however, the imidazole compounds according to this invention exert far better fungicidal action on fungi.

BRIEF SUMMARY OF THE INVENTION

The novel 1-benzoylhalomethylimidazole compounds according to this invention are represented by the following formulae:

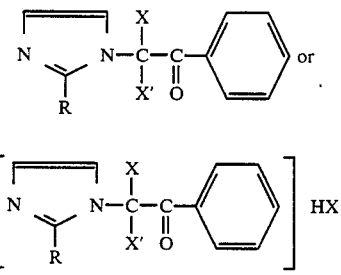

wherein R is a hydrogen atom or a lower alkyl group, X is a halogen atom and X' is a hydrogen atom or a halogen atom.

The novel 1-benzoylhalomethylimidazole compounds according to this invention are produced by reacting an imidazole compound represented by the formula

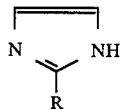

wherein R is a hydrogen atom or a lower alkyl group, with a halogenated acetophenone, and by reacting the 1-benzoylmethylimidazole with halogen.

The compounds according to this invention are very useful as antifungal agents, insect attractants and the like.

Referring to the properties of these novel compounds, they are weak acid white crystalline substances, insoluble in ether, chloroform, ethyl acetate, acetonitrile, xylene, dioxane, carbon tetrachloride and benzene, and very sparingly soluble in water and ethanol. On the other hand, they are soluble in methanol, pyridine and dimethyl sulfoxide.

Referring more in detail to the process for producing the novel compounds of this invention, 0.2 to 6 mol of e.g. imidazole or alkyl imidazole and 1 mol of halogenated acetophenone are mixed and reacted in a solvent such as methanol, ethanol, isopropyl alcohol, benzene, acetone, dimethyl formamide or the like at a temperature of 5° to 80° C. The reaction mixture is poured into the mixture of water and benzene, agitated therein and maintained under a cooling condition with ice. Then, the precipitated crystals of 1-benzoylmethylimidazole compound are filtered. The filter cake is recrystallized by a solvent such as benzene or the like, and dissolved in a mixed solution of halogenated hydrogen acid and acetic acid. Subsequently, a mixed solution of halogen and acetic acid is dropped into the aforesaid dissolved solution while maintaining the liquid temperature of 30° to 90° C. Further, after dropping, agitation is continued for 1 to 4 hours within this temperature range. The acetic acid is removed by distillation, and ether, ethyl acetate or a mixture thereof is added to the residue. Then, the crystals of 1-benzoylhalomethylimidazole are precipitated.

The novel 1-benzoylhalomethylimidazole compound is recovered by filtration and recrystallization using a solvent such as methanol, ethanol, acetonitrile or the like.

PREFERRED EXAMPLES OF THE INVENTION

Preferred examples of this invention will be described hereinafter.

EXAMPLE 1

A process for producing a 1-benzoylmonobromomethylimidazole hydrogen bromide salt will be described hereinafter.

700 grams of imidazole were agitated and added little by little into 500 ml of dimethyl formamide maintained at the temperature of 5±1° C. Subsequently, 400 grams of β-bromoacetophenone were added thereinto with agitation at the temperature of 8° to 12° C. The reaction mixture was added to a mixture of water 5 l and benzene 1 l, and the mixed solution was agitated two hours under cooling with ice. The precipitated crystals were filtered and recrystallized with benzene. As a result, 237 grams of 1-benzoylmethylimidazole having a melting point of 107° to 113° C. were produced. The yield as 63.7% based on the imidazole. And then, 186 grams of the 1-benzoylmethylimidazole were dissolved in a mixture of 172 grams of 47% hydrobromic acid and 800 ml of acetic acid. While maintaining the liquid temperature at 80° C. a mixture of 160 grams of bromine and 100 ml of acetic acid was dropped into the aforesaid mixture with agitation. After continuing agitation for three hours, the acetic acid was removed by distillation. Subsequently, the crystals were precipitated by adding ethyl acetate to the residue. After filtration, the filter cake was recrystallized with ethanol and 270.9 grams of white crystals having a melting point of 217° to 220° C. obtained. The results of analysis were showed that the product was 1-benzoylmonobromomethylimidazole hydrogen bromide salt. The yield was 78.3% of a theoretical ratio based on the imidazole.

The following was the result of analysis:

Elemental analysis: ($C_{11}H_9N_2O$ Br·HBr). Values as the result of analysis: C: 38.12%, H: 2.86%, N: 7.72%.

Thin Layer Chromatography [TLC] (Kiesselgel 60F254) Rate of flow: 0.76 (Benzene methanol 1:1, I$_2$ emission of color).

Infrared absorption spectroscopic analysis (cm$^{-1}$): 1705 (C=O) 1190, 1165, 1445 (CHBr). 1265 (CN), 600, 670 (Br).

Nuclear Magnetic Resonance [NMR] (PPM) 2'—H: 9.20, 4'—H: 8.06, 5'—H: 8.10—CH—: 5.71,

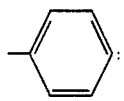

7.46–7.85.

EXAMPLE 2

A process for producing a 1-benzoylmonobromomethyl-2-methylimidazole hydrogen bromide salt will be described hereinafter.

492 grams of 2-methlylimidazole and 400 g of β-bromoacetophenone were agitated and added into 500 ml of dimethyl formamide. The crystals produced in the same manner as described in Example 1 were recrystallized with benzene and 246.4 grams of 1-benzoylmethyl-2-methylimidazole having a melting point of 138° to 140° C. were obtained. The yield was 61.3% based on imidazole.

Then, 200 grams of the 1-benzoylmethyl-2-methylimidazole were dissolved in a mixture of 172 grams of 47% hydrobromic acid and 800 ml of acetic acid, and the reaction mixture was added into the mixture of 160 grams of bromine and 100 ml of acetic acid in the same manner as Example 1. The thus produced crystals were recrystallized with methanol and white crystals having a melting point of 211° to 216° C. were obtained. The results of analysis showed that the product was 1-benzoylmonobromomethyl-2-methylimidazole hydrogen bromide salt. The yield was 80.5% based on 2-methylimidazole.

The following was the result of the analysis:

Elemental analysis: (C$_{12}$H$_{11}$N$_2$O Br·HBr). Values as the result of analysis: C: 40.69%, H: 3.34%, N: 7.46%. Calculated values: C: 40.02%, H: 3.34%, N: 7.76%.

Thin Layer Chromatography [TLC] Rate of flow: 0.71 (Benzene-methanol 1:1, I$_2$ emission of color).

Infrared absorption spectroscopic analysis (cm$^{-1}$). 1709 (c=O), 1190, 1180, 1165, 144 5 (CHBr), 1245 (CN), 640, 580 (Br).

EXAMPLE 3

A process for producing 1-benzoyldibromomethyl-2-methylimidazole will be described hereinafter.

200 gramns of the 1-benzoylmethyl-2-methylimidazole produced of Example 2 were dissolved in a mixed solution of 172 grams of 47% hydrobromic acid and 800 ml of acetic acid. After the temperature of the mixed solution reached 55° C., the mixture of 160 grams of bromine and 100 ml of acetic acid was dropped therein with agitation. At a temperature of 55° C., the agitation of the solution was continued for two days. Then, the acetic acid was removed by distillation and the mixture of ethyl acetate and ether was added to the residue.

Then, the crystal was precipitated. After filtering, the filter cake was recrystallized by acetonitrile and 141.7 grams of white crystals having a melting point of 200° to 201° C. was obtained.

The results of analysis showed that the product was 1-benzoyldibromomethyl-2-methylimidazole. The yield was 39.6% of the theoretical value based on 2-methylimidazole.

Elemental analysis: (C$_{12}$H$_{10}$N$_2$O Br$_2$). Values as the result of analysis: C: 40.33%, H: 3.50%, N: 8.04%. Calculated values: C: 39.92%, H: 2.79%, N: 7.76%.

Thin Layer Chromatography [TLC] Rate of flow: 0.75 (Benzene-methanol 1:1, I$_2$ emission of color).

Infrared absorption spectroscopic analysis (cm$^{-1}$): 1705 (C=O), 1160 (CBr$_2$), 1245 (CN), 640, 580, 560 (Br).

Nuclear Magnetic Resonance [NMR] (PPM) 2'—CH: 2.57, 4'—H: 8.06, 5'—H: 8.22

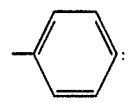

7.31–7.81.

EXAMPLE 4

With regard to each of the 1-benzoylbromomethylimidazole compounds as prepared according to Examples 1 to 3, their minimum concentration for preventing fungi were measured.

The test result was as follows.

| | Examined fungi | |
|---|---|---|
| Testing compounds | Trichophyton tonsurans | Trichophyton rubram |
| [N⟍N—CH(Br)—C(=O)—C$_6$H$_5$] HBr | <80 | 25 |
| [N⟍(CH$_3$)N—CH(Br)—C(=O)—C$_6$H$_5$] HBr | <80 | 40 |
| N⟍(CH$_3$)N—C(Br)$_2$—C(=O)—C$_6$H$_5$ | 1.25 | 1.25 |

The numerical unit of the minimum concentration for preventing the fungi is μg/ml.

What is claimed is:

1. 1-benzoyldibromomethyl-2-methylimidazole.

* * * * *

UNITED STATES PATENT AND TRADEMARK OFFICE
CERTIFICATE OF CORRECTION

PATENT NO. : 4,577,032
DATED      : March 18, 1986
INVENTOR(S): Takayuki Fujita et al It is certified that error appears in the above-identified patent and that said Letters Patent is hereby corrected as shown below:

On the title page, insert:

Assignee:  Shikoku Chemical Corporation
           Kagawa-ken, Japan

Signed and Sealed this

Eighth Day of July 1986

[SEAL]

Attest:

DONALD J. QUIGG

Attesting Officer

Commissioner of Patents and Trademarks